United States Patent
Topsøe

[11] Patent Number: 5,455,281
[45] Date of Patent: Oct. 3, 1995

[54] METHOD OF COOLING A SYNTHESIS GAS IN A CATALYTIC REACTOR

[75] Inventor: Haldor F. A. Topsøe, Vedbaek, Denmark

[73] Assignee: Haldor Topsoe A/S, Denmark

[21] Appl. No.: 163,121

[22] Filed: Dec. 7, 1993

[30] Foreign Application Priority Data

Dec. 7, 1992 [DK] Denmark ............................. DK465/92

[51] Int. Cl.⁶ .................................................. C07C 27/06
[52] U.S. Cl. .......................... 518/707; 518/706; 518/712
[58] Field of Search .................................. 518/706, 707, 518/712

[56] References Cited

U.S. PATENT DOCUMENTS 2,512,586   6/1950   Stengel ..................................... 518/712
4,963,338  10/1990   Zardi et al. ............................. 518/712

FOREIGN PATENT DOCUMENTS 1159035   7/1969   United Kingdom .

*Primary Examiner*—Johann Richter
*Assistant Examiner*—Kimberly J. Kestler
*Attorney, Agent, or Firm*—Ostrolenk, Faber, Gerb & Soffen

[57] ABSTRACT

Method of direct cooling synthesis gas in a catalytic reactor with one or more catalyst beds of a metal oxide catalyst being loaded on gas permeable partitions with distribution means, which method comprises admixing the synthesis gas during its passage through the reactor with a cooling gas being introduced into a mixing zone beneath each partition, wherein the mixing zones are obtained by passing a reducing gas through the catalyst bed, so that the catalyst volume shrinks during reduction of the catalyst particles, and, thereby, providing necessary cavities for the mixing zones beneath each partition.

7 Claims, No Drawings

METHOD OF COOLING A SYNTHESIS GAS IN A CATALYTIC REACTOR

The present invention relates to a method of cooling a synthesis gas in catalytic reactions. In particular, the invention is concerned with cooling of synthesis gas in exothermic conversion processes by a cooling gas, which is added to the synthesis gas during its passage through the reactor.

Catalytic processes are usually carried out in a reactor with one or more beds of catalyst particles. A large number of those processes proceed exothermically with considerable heat generation. It is necessary to remove heat evolving during the catalytic reactions at least from parts of the catalyst bed in order to maintain a desired conversion rate and to avoid destruction of the catalyst.

This is conventionally carried out by indirect cooling of the reacting synthesis gas through heat exchange with a cooling medium or by direct cooling with introduction of a cooling gas, usually fresh synthesis gas, into the catalyst bed through distribution aggregates. In many reactors, the catalyst is arranged as a continuous bed in the reactor, and cooling gas is distributed within the catalyst bed.

The known methods of direct cooling of reacting synthesis gas disadvantageously demand expensive reaction volume to provide necessary space for distributing or admixing cooling gas and synthesis gas between or within the catalyst beds.

When introducing cooling gas directly within the catalyst bed, the stream of cooling gas is poorly distributed within the bed resulting in local flow variations and varying mixing ratios of cooling gas and synthesis gas.

Further drawback of conventional designed reactors is poor utilization of the expensive pressure shell, high pressure drop, and formation of by-products because of disintegration of the catalyst particles and insufficient cooling of parts of the catalyst bed.

It is, therefore, often desired to revamp conventional designed reactors employing direct cooling of synthesis gas, to avoid the above problems and to obtain higher production capacity.

It has been found that the problems and disadvantages of conventionally cooled reactors may be avoided when utilizing shrinkage of the catalyst volume occurring during activation of many catalyst types, leading to cavities formed in the activated catalyst. Those cavities may conventionally be utilized for introduction and admixing of cooling gas in the residual gas stream without wasting expensive reactor volume.

Shrinkage of the catalyst volume occurs when reducing metal oxide components in the catalyst particles by contact with reducing gas, which is passed through the reactor during activation of the catalyst.

This invention provides a method of direct cooling synthesis gas in a catalytic reactor with one or more catalyst beds of a metal oxide catalyst being loaded on gas permeable partition with distribution means, which method comprises admixing the synthesis gas during its passage through the reactor with a cooling gas being introduced into a mixing zone beneath each partition. The mixing zones are obtained by passing a reducing gas through the catalyst beds, so that the catalyst volume shrinks during the reduction of the catalyst particles, thereby providing necessary cavities for the mixing zones beneath each partition.

In practice, the invention is carried out by arranging within a reactor one or more partitions connected or provided with gas distribution and mixing aggregates, and loading the space between the partitions with non-activated catalyst particles. After the catalyst particles are loaded, reducing gas of e.g. mixtures of hydrogen and nitrogen is passed through the catalyst beds. Thereby, metal oxides in the catalyst are reduced to their metallic form, which causes the catalyst volume to shrink.

The invention is particularly useful in the performance of cooled exothermic processes, being catalyzed by the above catalyst types, and, in particular, catalytic synthesis of methanol by exothermic conversion of carbon oxides and hydrogen in contact with a metal oxide catalyst usually consisting of zinc oxide, copper oxide, chromium oxide and aluminium oxide. These metal oxides shrink up to 20 volume per cent during activation of the catalyst by reduction of the metal oxides.

The invention may further be used with catalysts, which show no or only minor shrinkage during activation as described above. Those catalysts are mixed with or provided with separately arranged particles, which shrink or otherwise being removed from the catalyst bed during activation without being catalytic active in the subsequent synthesis process.

I claim:

1. Method of direct cooling of synthesis gas in a catalytic exothermic reaction carried out in a reactor with one or more catalyst beds of a metal oxide catalyst, which method comprises
   (a) passing a reducing gas through said metal oxide catalyst beds, said catalyst being loaded between gas permeable partitions without a space between the beds, thereby reducing metal oxide catalyst to its metallic form, said metallic form having a smaller volume than the metal oxide, whereby the total volume of each catalyst bed between the partitions shrinks, leaving a void volume beneath each partition, said void volume constituting a mixing zone; and
   (b) admixing the synthesis gas during its passage through the reactor with a cooling gas, said cooling gas being introduced into said mixing zone beneath each partition.

2. The method of claim 1, wherein the cooling gas is fresh synthesis gas.

3. The method of claim 1, wherein the synthesis gas comprises carbon oxides and hydrogen for use in preparation of methanol.

4. Method of providing mixing zones for mixing a cooling gas and synthesis gas in a gas cooled catalytic reactor having one or more catalyst beds of a metal oxide catalyst loaded between gas permeable partitions equipped with means for distributing the cooling gas into said mixing zones, which method comprises passing a reducing gas through the catalyst beds prior to passage of the synthesis gas and cooling gas, thereby reducing metal oxide catalyst to its metallic form, said metallic form having a smaller volume than the metal oxide, whereby the total volume of each catalyst bed between the partitions shrinks, leaving a void volume for the mixing zone downstream of each partition.

5. The method of claim 2, wherein the synthesis gas comprises carbon oxides and hydrogen for use in preparation of methanol.

6. The method of claim 3, wherein the metal oxide catalyst consists of zinc oxide, copper oxide, chromium oxide and aluminum oxide.

7. The method of claim 4, wherein the metal oxide catalyst consists of zinc oxide, copper oxide, chromium oxide and aluminum oxide.

* * * * *